United States Patent
Zhao (10) Patent No.: US 11,352,390 B2
(45) Date of Patent: Jun. 7, 2022

(54) PEPTOID COMPOUND AND PREPARATION METHOD, CARRIER, AND PHARMACEUTICAL COMPOSITION THEREOF

(71) Applicants: BEIJING BOE TECHNOLOGY DEVELOPMENT CO., LTD., Beijing (CN); BOE TECHNOLOGY GROUP CO., LTD., Beijing (CN)

(72) Inventor: Zijian Zhao, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 282 days.

(21) Appl. No.: 16/633,321

(22) PCT Filed: Jan. 3, 2019

(86) PCT No.: PCT/CN2019/070261
§ 371 (c)(1),
(2) Date: Jan. 23, 2020

(87) PCT Pub. No.: WO2020/140237
PCT Pub. Date: Jul. 9, 2020

(65) Prior Publication Data
US 2021/0246163 A1    Aug. 12, 2021

(51) Int. Cl.
| C07K 7/06 | (2006.01) |
| A61K 38/08 | (2019.01) |
| A61K 47/34 | (2017.01) |
| A61K 47/42 | (2017.01) |
| C07K 1/04 | (2006.01) |

(52) U.S. Cl.
CPC ............... *C07K 7/06* (2013.01); *A61K 47/34* (2013.01); *A61K 47/42* (2013.01); *C07K 1/04* (2013.01)

(58) Field of Classification Search
None
See application file for complete search history.

(56) References Cited

FOREIGN PATENT DOCUMENTS

| CN | 101501065 A | 8/2009 |
| CN | 105753940 A | 7/2016 |
| CN | 106854233 A | 6/2017 |
| CN | 106866794 A | 6/2017 |

(Continued)

OTHER PUBLICATIONS

First Chinese Office Action from Chinese Patent Application No. 201980000007.4 dated Mar. 30, 2022.

*Primary Examiner* — Kevin S Orwig
(74) *Attorney, Agent, or Firm* — Dilworth & Barrese, LLP.; Michael J. Musella, Esq.

(57) ABSTRACT

A peptoid compound, a nanometer carrier, a pharmaceutical composition, and use of the pharmaceutical composition in manufacture of a medicament for treatment of a disease related to human epidermal growth factor receptor 1 (EGFR). The peptoid compound includes: cysteine (Cys) subunit, 1,4-butanediamine (Nlys) subunit, piperonylamine subunit, β-alanine subunit and 1-naphthylamine subunit. The peptoid compound has high affinity and targeting effect to the EGFR protein, and high selectivity, and meanwhile has high medicament loading efficiency, no toxicity, and high safety.

11 Claims, 3 Drawing Sheets

(56) References Cited

FOREIGN PATENT DOCUMENTS

| CN | 108653242 A | | 10/2018 | | |
|---|---|---|---|---|---|
| WO | 2012125904 A1 | | 9/2012 | | |
| WO | 106854233 | * | 6/2017 | ............... | C07K 7/06 |

* cited by examiner

PEPTOID COMPOUND AND PREPARATION METHOD, CARRIER, AND PHARMACEUTICAL COMPOSITION THEREOF

TECHNICAL FIELD

Embodiments of the present disclosure relate to a peptoid compound, a preparation method of the peptoid compound, a nanometer carrier, a pharmaceutical composition, and use of the pharmaceutical composition in the preparation of a medicament for the treatment of a disease related to human epidermal growth factor receptor 1 (EGFR).

BACKGROUND

Neuroepithelium-derived tumors are collectively known as gliomas, and the gliomas accounts for 40% to 50% of brain tumors. The gliomas are the most common intracranial malignant tumors, with an annual incidence of 3 to 8 persons per 100,000 persons. Lung cancer is currently the cancer with the highest incidence and mortality, and brain metastases of the lung cancer and the lung cancer caused by blood-brain barrier factor become more difficult to be cured.

Targeted therapy and living imaging of cancer have become one of the most popular topics in academia and clinical medicine. Currently, cytotoxic chemotherapeutic drugs are mainly used in clinic for antitumor. However, such drugs have poor selectivity and high toxicity side effect, which tend to cause adverse reactions. Although protein drugs such as antibodies have good specificity and low toxicity side effects, they are easy to cause immune reaction and drug resistance due to their large molecular weight and complicated structure, and their preparation process is so complicated that the price is too expensive to be borne by ordinary patients with tumor.

SUMMARY

At least one embodiment of the present disclosure provides a peptoid compound, and the peptoid compound comprises: a cysteine (Cys) subunit, a 1,4-butanediamine (Nlys) subunit, a piperonylamine subunit, a β-alanine subunit, and a 1-naphthylamine subunit.

For example, in the peptoid compound provided by at least one embodiment of the present disclosure, the peptoid compound comprises the subunits in a sequence of: cysteine (Cys) subunit-1,4-butanediamine (Nlys) subunit-1,4-butanediamine (Nlys) subunit-piperonylamine subunit-4-butanediamine (Nlys) subunit-β-alanine subunit-1-naphthylamine subunit.

For example, in the peptoid compound provided by at least one embodiment of the present disclosure, the peptoid compound has a structure as represented by:

Formula I

At least one embodiment of the present disclosure further provides a preparation method of the peptoid compound according to any one of the embodiments mentioned above, which comprises linking the subunits by a solid-phase synthesis process.

For example, the preparation method of the peptoid compound provided by at least one embodiment of the present disclosure, comprises:
(1) linking a first subunit of the peptoid compound onto a solid-phase carrier in accordance with the linking sequence of the subunits of the peptoid compound;
(2) reacting bromoacetic acid or bromoacetyl chloride with an amino group of the first subunit linked onto the solid-phase carrier to form an amide bond;
(3) reacting a donor for a second subunit of the peptoid compound with a product obtained from step (2) to replace a bromine atom and complete the linking of the second subunit;
(4) repeating steps (2) and (3) until all subunits are linked; and
(5) cleaving the synthesized peptoid compound from the solid-phase carrier to obtain the peptoid compound.

At least one embodiment of the present disclosure further provides a nanometer carrier, and the nanometer carrier comprises any one of the peptoid compounds according to the embodiments mentioned above, a polyamidoamine dendrimer (PAMAM), and polyethylene glycol (PEG), in which the polyethylene glycol (PEG) links the peptoid compound to the polyamidoamine dendrimer (PAMAM).

For example, in the nanometer carrier provided by at least one embodiment of the present disclosure, a molar ratio of the peptoid compound to the polyamidoamine dendrimer (PAMAM) is from 1:5 to 1:1, and a molar ratio of the PEG to the PAMAM is from 1:25 to 1:35.

For example, in the nanometer carrier provided by at least one embodiment of the present disclosure, a generation number of the polyamidoamine dendrimer (PAMAM) is 4 or greater than 4.

At least one embodiment of the present disclosure further comprises a pharmaceutical composition, and the pharmaceutical composition comprises any one of the nanometer carriers mentioned above and a pharmaceutically acceptable adjuvant.

For example, in the pharmaceutical composition provided by at least one embodiment of the present disclosure, the pharmaceutically acceptable adjuvant comprises any one or at least two of an excipient, a diluent, a carrier, a flavoring agent, an adhesive, and a filler.

At least one embodiment of the present disclosure further provides use of any one of the pharmaceutical compositions mentioned above in the preparation of a medicament for the treatment of a disease related to human epidermal growth factor receptor 1 (EGFR).

For example, in the use provided by at least one embodiment of the present disclosure, the disease comprises glioma and brain metastases of lung cancer.

BRIEF DESCRIPTION OF THE DRAWINGS

In order to clearly illustrate the technical solution of the embodiments of the present disclosure, the drawings of the embodiments will be briefly described. It is apparent that the described drawings are only related to some embodiments of the present disclosure and thus are not limitative of the present disclosure.

REFERENCE NUMBERS

Figure 2:
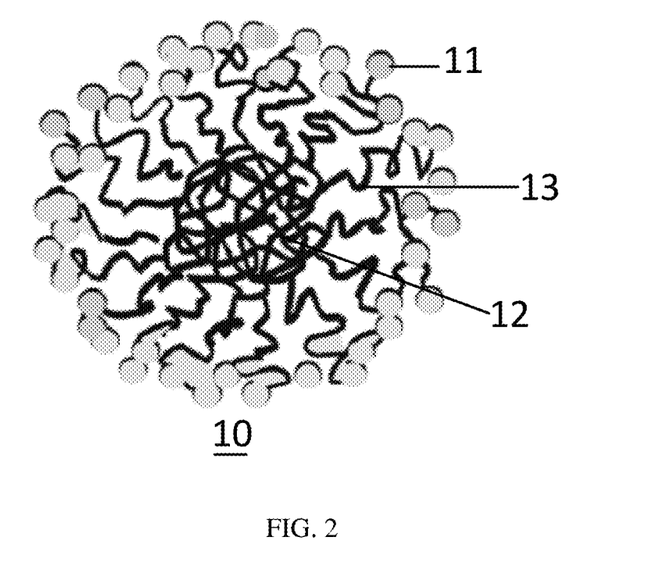
FIG. 2 is a structural schematic view of a nanometer carrier provided by an embodiment of the present disclosure.

10—nanometer carrier; 11—peptoid compound; 12—polyamidoamine dendrimer (PAMAM); 13—polyethylene glycol (PEG).

DETAILED DESCRIPTION

In order to make objects, technical details and advantages of embodiments of the disclosure clear, the technical solutions of the embodiments will be described in a clearly and fully understandable way in connection with the related drawings. It is apparent that the described embodiments are just a part but not all of the embodiments of the disclosure. Based on the described embodiments herein, those skilled in the art can obtain, without any inventive work, other embodiment(s) which should be within the scope of the disclosure.

Unless otherwise defined, all the technical and scientific terms used herein have the same meanings as commonly understood by one of ordinary skill in the art to which the present invention belongs. The terms "comprises," "comprising," "includes," "including," etc., are intended to specify that the elements or the objects stated before these terms encompass the elements or the objects listed after these terms as well as equivalents thereof, but do not exclude other elements or objects. The monomer used in the present disclosure refers to material amine added during the solid-phase synthesis of the peptoid compound. The subunit in the present disclosure refers to structural units of the peptoid compound.

Unless specially indicated, "EGFR" in the present disclosure refers to a human epidermal growth factor receptor 1.

Unless specially indicated, "nM" refers to "nmol /L", "μM" refers to "μmol/L", and "mM" refers to "mmol/L" in the present disclosure.

By means of enhanced permeability and retention effect (EPR) of solid tumors, drugs can be delivered by a novel drug carrier to tumor sites in a passive targeting manner. By using specific recognition elements, specific targeted administration enables the drug to be selectively and actively concentrated in the tumor sites, and thus increases the concentration of the drug and enhances the penetrating effect, thereby significantly improving the therapeutic effect. Living imaging is achieved by using recognition elements as the main body, in combination with imaging means such as fluorescence and nuclear magnetic resonance (NMR). Thus, the recognition elements are the most important portion of the whole targeting drug and the living imaging. For example, the recognition elements comprise targeting molecules for tumor site specific receptor, such as antibodies, polypeptides, peptoids, and aptamers. Among various targeting molecules, aptamers have particular advantages such as low immunogenicity, good tissues permeability, low molecular weight, high stability, modification easiness, and low cost.

At least one embodiment of the present disclosure provides a peptoid compound, and the peptoid compound comprises: cysteine (Cys) subunit, 1,4-butanediamine (Nlys) subunit, piperonylamine subunit, β-alanine subunit and 1-naphthylamine subunit.

It should be noted that, the peptoid compound is a peptide mimetic having N-substituted glycine as a structural unit. Compared with peptide compounds, side chains of the peptoid compounds are transferred from α-carbon to nitrogen. Different from traditional peptide compounds which are composed of only 20 kinds of amino acids, the peptoid compound is synthesized by a monomer synthesis process and its constituent units are determined by different amines. There are thousands of amines, and thus the peptoid compounds have extremely abundant sequences. It is possible to develop different chemical sequence structures for different targets. Moreover, because the peptoid compounds are not recognized by enzymes, the peptoid compounds can effectively resist proteolysis in vivo, which makes the peptoid compound have more obvious advantages as a molecular probe.

The drug delivery system and the molecular imaging system developed based on the peptoid compound molecular probe can enhance the stability of drugs, increase an interaction between drugs and tumor cells/tissues, and increase the circulating metabolic cycle in vivo. Therefore, it has advantages in terms of in vivo imaging diagnosis, drug efficacy enhancement, overcoming of drug resistance, and reduction of toxicity side effects. 100331 For example, the peptoid compound provided by at least one embodiment of the present disclosure comprises the subunits in a sequence of: cysteine (Cys) subunit-1,4-butanediamine (Nlys) subunit-1,4-butanediamine (Nlys) subunit-piperonylamine subunit-1,4-butanediamine (Nlys) subunit-β-alanine subunit-1-naphthylamine subunit.

For example, the peptoid compound provided by at least one embodiment of the present disclosure is the compound of Formula I or a pharmaceutically acceptable salt thereof.

For example, the above mentioned peptoid compounds can specifically recognize the full-length human epidermal grow factor receptor 1 (an EGFR protein), and can realize targeted drug delivery of EGFR high expression glioma or lung cancer brain metastasis with lower cost, more accuracy and more efficiency.

Formula I

For example, in at least one embodiment of the present disclosure, the peptoid compound is the compound of Formula I.

The term "stereoisomer" belongs to a kind of isomers, and refers to isomers that have the same interconnecting orders of atoms or atomic groups, but different spatial arrangements.

As for the stereoisomer, the compound of Formula I has an asymmetric carbon atom, which can exist as an enantiomer or as a mixture of enantiomers, such as a racemic mixture or a mixture enriched with one enantiomer. Embodiments of the present disclosure cover any stereoisomer of a compound of formula I or a pharmaceutically acceptable salt thereof and mixtures of various forms thereof.

For example, in the embodiments of the present disclosure, the peptoid compound exists in a form of salt. For example, the salt can be prepared by reacting the peptoid compound with an inorganic acid or an organic acid. The inorganic acid, for example, is hydrochloric acid, hydrobromic acid, sulfuric acid, nitric acid or phosphoric acid, and so on. The organic acid, for example, is formic acid, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid or salicylic acid, and so on.

For example, in the embodiments of the present disclosure, the salt for example, is a pharmaceutically acceptable salt. For example, the pharmaceutically acceptable salt is hydrochloride, hydrobromide, sulfate, nitrate, phosphate, formate, acetate, propionate, fumarate, glycolate, pyruvate, malate, malonate, benzoate, cinnamate, mandelate, salicylate, maleate, citrate, succinate, tartrate, mesylate, ethanesulfonate, or p-toluenesulfonate.

For instance, in the embodiments of the present disclosure, the pharmaceutically acceptable salt is hydrochloride, nitrate, sulfate, formate, acetate, fumarate, maleate, citrate, succinate, tartrate, mesylate, or p-toluene sulfonate.

At least one embodiment of the present disclosure further provides a preparation method of the peptoid compound according to any one of the embodiments mentioned above, which comprises linking the subunits by a solid-phase synthesis process.

Figure 1:
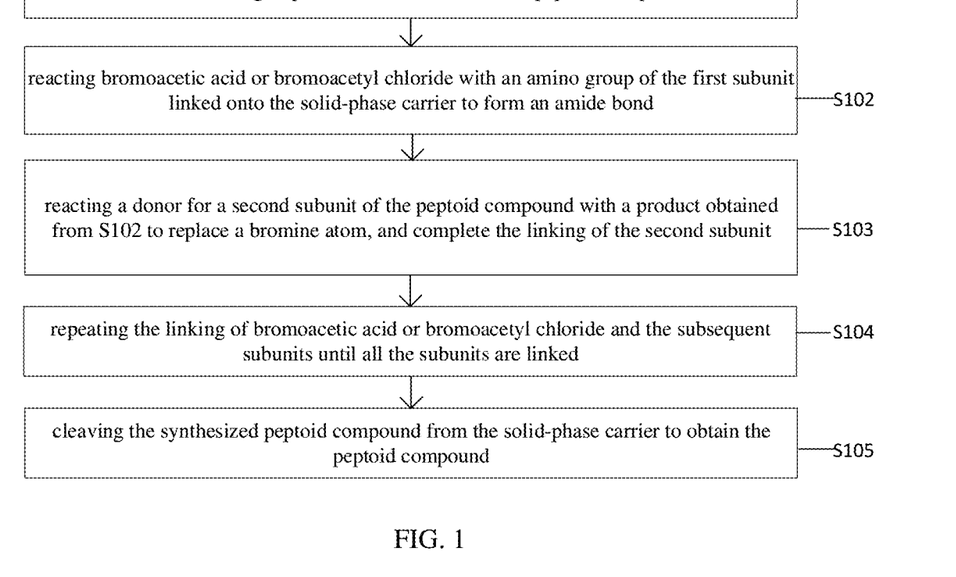
FIG. 1 is a flowchart of a preparation method of a peptoid compound provided by an embodiment of the present disclosure.

For example, FIG. 1 is a flowchart of a preparation method of a peptoid compound provided by an embodiment of the present disclosure, and the preparation method comprises the following steps.

S101: linking a first subunit of the peptoid compound onto a solid-phase carrier in accordance with the linking sequence of the subunits of the peptoid compound.

S102: reacting bromoacetic acid or bromoacetyl chloride with an amino group of the first subunit linked onto the solid-phase carrier to form an amide bond.

S103: reacting a donor (monomer) for a second subunit of the peptoid compound with a product obtained from S102 to replace a bromine atom, and complete the linking of the second subunit.

S104: repeating S102 and S103 until all subunits are linked, in which the monomers are fed in an order of: cysteine, mono-protected 1,4-butanediamine, mono-protected 1,4-butanediamine, piperonylamine, mono-protected 1,4-butanediamine, β-alanine and 1-naphthylamine, and the term "mono-protected" means that one amino group of the diamine is protected by an amino-protecting group.

For example, as the amino-protecting group of the diamine, any groups that are known in the art for using in protection of amino during synthesis of protein, peptide, or peptoid compounds can be used without limitation. For example, the amino-protecting group is 9-fluorenylmethoxycarbonyl (Fmoc) or t-butoxycarbonyl (Boc). For instance, the amino-protecting group in some embodiments is the t-butoxycarbonyl.

S105: cleaving the synthesized peptoid compound from the solid-phase carrier to obtain the peptoid compound.

The peptoid compound of the present disclosure is prepared as a single enantiomer or a racemic mixture by selecting raw materials. For example, in the process of preparing the peptoid compound of the present disclosure, the raw material of cysteine is selected from the group consisting of D-cysteine, L-cysteine, or a mixture of D-cysteine and L-cysteine.

The peptoid compound in the embodiments of the present disclosure can also he separated by chiral resolution, for example, by chiral HPLC to obtain a single enantiomer.

For example, in a case that bromoacetic acid reacts with the amino of the first subunit linked to the solid-phase carrier to form the amido bond, the reaction scheme of S102 and S103 are as follows:

Reaction formula 1

For example, in a case that bromoacetyl chloride reacts with the amino of the first subunit linked to the solid-phase carrier to form the amide bond, the reaction scheme of S102 and S103 are as follows:

Reaction formula 2

For example, the reaction conditions of the amidation reaction in step S102 are not particularly limited. The conventional conditions for the amidation reaction for the synthesis of protein, polypeptide or peptoid compound in the art can be used as long as the amino can be acylated and the function of the peptoid compound is not damaged. For example, the amidation reaction is carried out in the presence of a condensation agent. The condensation agent is known in the art for using in the synthesis of protein, polypeptide or peptoid compound. For example, the condensation agent is a carbodiimide-based condensation agent, for example, N,N'-diisopropyl carbodiimide (DIC), N,N'-dicyclohexylcarbodiimide (DCC) or 1-ethyl-(3-dimethyl-aminopropyl)carbodiimide (EDC) and so on; a benzotriazole-basest condensation agent, for example, 1-hydroxyl benzotriazole(HOBt); a benzenesulfonyl chloride-based condensation agent, for example, tri-isopropyl benzenesulfonyl chloride (TPS) and so on; a succinimide-based condensation agent, for example, disuccinimido carbonate (DSC), succinimido diphenyl phosphate (SDPP) and so on; 2-ethoxy-1-ethoxycarbonyl-1,2-dihydroquinoline (EEDQ); or 3-(diethoxyphosphoryloxy)-1,2,3-benzotriazin-4(3H)-one (DEPBT) and so on.

The reaction conditions of the nucleophilic substitution in the step S103 are not particularly limited, and conventional nucleophilic substitution conditions for using in the synthesis of proteins, polypeptides, or peptoids can be used, as long as the bromine atom can he replaced and the function of the peptoid compound is not damaged. For example, the reaction is carded out at a temperature of 35° C. to 40° C. for 30 minutes or more, 60 minutes or more, or 90 minutes or more.

In the step S105, the removal of the side chain amino protection group and the cleavage of the peptoid compound from the resin can be carried out simultaneously or successively. For example, firstly, the peptoid compound is cleaved from the resin, and then the side chain amino protection group is removed; alternatively, the side chain amino protection group is removed firstly, and then the peptoid compound is cleaved from the resin; or the peptoid compound is cleaved from the resin while the side chain amino protection group is removed. The conventional conditions for synthesis of proteins, polypeptides or peptoids in the art can be used to remove the side chain amino protection group and cleave the peptoid compound from the resin, as long as the purpose can be achieved and the function of the peptoid compound is not damaged. In an embodiment, the peptoid compound is cleaved from the resin while the side chain amino protection group is removed by a cleaving solution containing 95% trifluoroacetic acid, 2.5% ultrapure water and 2.5% trisisopropylsilane at a volume ratio.

For example, the peptoid compound represented by Formula I is synthesized by the solid-phase synthesis process as follows:

(1) immersing rink amide AM resin (having a substitution level of 0.3 mmol/g, 200 mg) in N,N-dirnethylformamide (DMF), and discharging the DMF solution after 15 minutes of full swelling;

(2) deprotection: formulating a DMF solution comprising 20% by mass of hexahydropyridine, and immersing the resin into an excessive amount of deprotection solution for 10 min, so as to remove the protection group and expose the free amino;

(3) washing the resin: washing the resin alternately with dichloromethane (DCM) and DMF for three times each;

(4) adding 2 M of bromoacetic acid in DMF (2.5 ml) and 3.2 M of N,N'-diisopropyl carbodiimide (DIC) in DMF (2.5 ml) to the Rink amide AM resin, and reacting at 37° C. for 30 min to acylate the terminal amino of the resin;

(5) further adding 2 M of a monomer to be added in DMF (5 ml), and reacting at 37° C. for 90 min, so as to replace the bromine atom by nucleophilic substitution reaction and complete the synthesis of a subunit;

(6) washing the resin: washing the resin alternately with DCM and DMF for three times each;

(7) repeating steps (4) to (6) until the syntheses of the other subunits are completed; in which the monomers are fed in an order of: cysteine, mono-protected 1,4-butanediamine, mono-protected 1,4-butanediamine, piperonylamine, mono-protected 1,4-butanediamine, β-alanine and 1-naphthylamine;

(8) removing the side-chain protection group at the end of the synthesis, and cleaving the peptoid compound from the resin by treatment with 9.5 vol % trifluoroacetic acid, 2.5 vol % ultrapure water and 2.5 vol % triisopropylsilane for 2,5 hours; and (9) purifying the peptoid compound by HPLC after filtration, dilution, and lyophilization.

In the preparation method of the peptoid compound in the present disclosure, a, step of further purifying the product can be included if desirable. The purification method has no special limitations, and methods such as precipitation, filtration, dialysis, gel permeation chromatography and HPLC which are known in the field can be used to purify the corresponding product.

At least one embodiment of the present disclosure further provides a nanometer carrier. For example, FIG. 2 is a structural schematic view of a nanometer carder provided by an embodiment of the present disclosure. As illustrated in FIG. 2, the nanometer carrier 10 comprises: any one of the peptoid compounds 11 mentioned above, polyamidoamine dendrimer (PAMAM) 12, and polyethylene glycol (PEG) 13, in which the polyethylene glycol (PEG) 13 links the peptoid compound 11 to the polyamidoamine dendrimer (PAMAM) 12.

For example, in the nanometer carrier 10, a molar ratio of the peptoid compound 11 to poly amidoamine dendrimer (PAMAM) 12 is from 1:5 to 1:1.

For example, a molar ratio of PEG 13 to the PAMAM 12 is from 1:25 to 1:35. For example, the molar ratio of the PEG to the PAMAM is 1:30.

For example, some or all of the amino groups at the periphery of the PAMAM 12 are attached to one end of PEG13 molecules respectively, and molecules of the peptoid compound 11 are attached to the other end of some or all of the PEG13 molecules.

For example, molecules of the peptoid compound 11 are attached to the other end of some or all of the PEG13 molecules by chemical bonds.

For example, the PAMAM dendrimer is flexible, has a spheroidal structure in an aqueous solution, and has a "dense inside and sparse outside" structure, that is, the density decreases as the crystal phase distance increases. The PAMAM dendrimer has a wide range of application prospects in terms of drug carriers, nanocomposites, nanoreactors, capillary gas chromatography stationary phase, wastewater treatment, emulsion explosive stabilitzers, catalysts, rheology modifiers of polymeric materials, photoelectric sensors, liquid crystals, monomolecular membranes, and gene carriers.

For example, as a stable drug carrier, the polyamideamine dendrimer (PAMAM) coupled with the peptoid compound has advantages of easiness to design, synthesize and modify; good biocompatibility; high drug loading; low toxicity; and high drug delivery, and thus has a wide range of application prospects. High generation (for example, 4 generation or more than 4 generation) of the polyamideamine dendrimer changes the charge distribution by adjusting the pH in the aqueous solution, so as to act as a drug carrier by encapsulating a hydrophobic drug into the core. By means of physical encapsulation or chemical bonding, the drug is incorporated or bonded into the nanometer carrier formed by the polyamideamine dendrimer (PAMAM) coupled with peptoid compound. The drug achieves a sustained-release effect through degradation of the nanometer carrier itself or cleavage from the nanometer carrier, which increases the utilization of the drug, increases the drug targeting, and reduces the toxicity side effect of the drug.

For example, the PAMAM dendrimer has various charges at different pH. Under an acidic condition, the amines on the outermost layer of the PAMAM and the tertiary amines inside the PAMAM are all protonized, and have 126 positive charges in total. Under a neutral condition, only the amines on the outermost layer of the PAMAM are protonized, so that a generation IV dendrimer has 64 positive charges. Neither the drug encapsulated inside the PAMAM dendrimer nor the peptoid compound coupled to the outer layer of the PAMAM dendrimer carry electrostatic charge at the acidic condition and the neutral condition.

For example, around the cells of glioma or lung cancer brain metastasis target with high expression of EGFR, the pH is relatively low and slightly acidic so that the surface of the PAMAM dendrimer has more charges, and charged nanoparticles can penetrate into the cell membrane, and the ability of inducing the membrane to form cavities is also related to the size of nanoparticles.

For example, the peptoid compound 11 has a high affinity to the EGFR protein, a strong target effect to the EGFR protein, a high selectivity, a good drug loading efficiency without toxicity, and an improved security. Therefore, targeted drug delivery and location imaging can be realized by recognizing the EGFR protein. It provides a new choice for diagnosis and treatment of gliomas with high expression of EGFR, brain metastasis of lung cancer and other EGFR positive tumors, and further provides in vivo data support for sequencing and digital PCR results. New and more effective targeted anticancer drugs can be made by adding a pharmaceutically acceptable excipient or adjuvant.

For example, a generation number of the polyamidoamine dendrimer (PAMAM) is 4 or greater than 4. For example, the generation number of the polyamidoamine dendrimer (PAMAM) is 5 or 6 and so on. The higher the generation number of the polyamidoamine dendrimer (PAMAM), the more the branches, and the closer its form is to a sphere.

For example, the synthesis process of the nanometer carrier is as follows.

S201: synthesizing a polyamidoamine dendrimer (PAMAM)-polyethylene glycol (PEG), wherein PAMAM and PEG are available from a Sigma Company.

Taking a generation IV polyamideamine dendrimer (G4PAMAM) for example, methanol (MeOH) and dimethylsulfoxide (DMSO) with a molar ratio of 1:1 are mixed to form a mixed solvent; PEG is activated with N-hydroxylsuccinimide (NHS); and the PAMAM dendrimer and the activated PEG are mixed and then added into the mixed solvent; and the mixture is reacted at room temperature for 15 minutes to synthesize the PAMAM-PEG, which is purified by Sephadex G-50 column to remove unreacted PEG.

S202: synthesizing the peptoid compound.

The synthesis process of the peptoid compound can refer to the related descriptions for the above mentioned steps S101 to S105.

S203: using maleimide (available from a Sigma Company) to activate the PAMAM-PEG formed in the above step S201, and reacting the activated PAMAM-PEG with a certain proportion of the peptoid compound at room temperature to obtain the nanometer carrier.

For example, the reaction mechanism o the activated PAMAM-PEG reacting; with the peptoid compound is as follows.

-continued

PAMAM—[PEG]$_n$—CH$_2$CH$_2$—NH Peptoid

For example, maleimide (Mal)-activated PAMAM-PEG and the peptoid compound with a molar ratio of 1:15 are mixed to form a reaction mixture, and then the reaction mixture is continuously stirred at room temperature for 30 hours. The reaction mixture is dialyzed and lyophilized to obtain the nanometer carrier.

Figure 3:
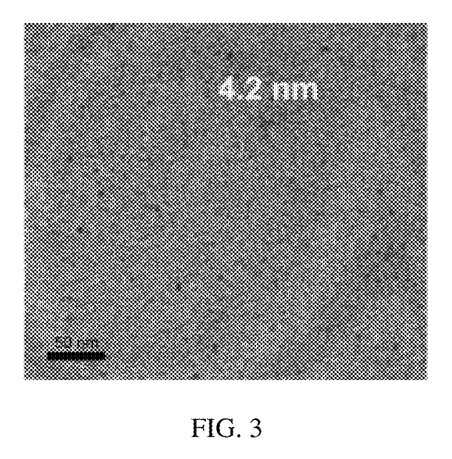
FIG. 3 is a scanning electron microscopy (SEM) image of a nanometer carrier provided by an embodiment of the present disclosure.

For example, FIG. 3 is a scanning electron microscopy (SEM) image of a nanometer carrier provided by an embodiment of the present disclosure. It can be seen from FIG. 3, the nanometer carrier is spherical, and an average particle size of the nanometer carrier is about 4.2 nm. The nanometer carrier having the size can easily enter into a cell membrane.

Figure 4:
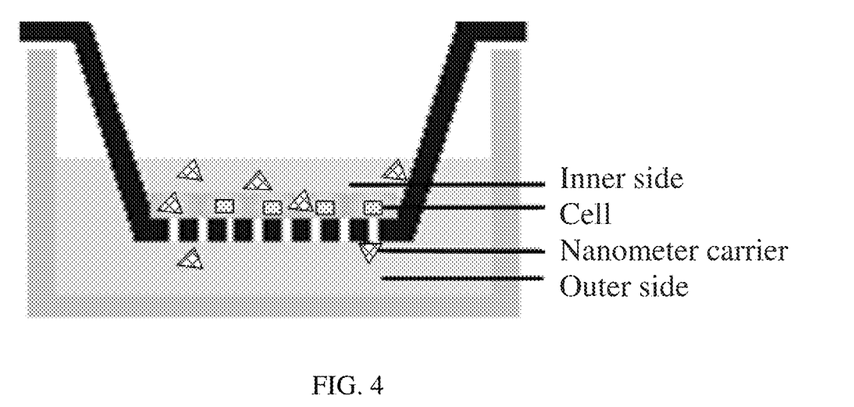
FIG. 4 is a schematic diagram of the capacity of a nanometer carrier provided by an embodiment of the present disclosure to penetrate a blood-brain barrier.

For example, by establishing a blood-brain barrier model, the capacity of a drug to penetrate the blood-brain barrier is able to be verified. FIG. 4 schematically shows the capacity of a nanometer carrier to penetrate the blood-brain barrier provided by an embodiment of the present disclosure. As illustrated in FIG. 4, the blood-brain harder comprises an inner side and an outer side. Cells and labelled nanometer carriers are formed at the inner side of the blood-brain barrier. The blood-brain barrier, the cells, and the labelled nanometer carriers are all placed in a culture medium. A penetration efficiency of the nanometer carriers is calculated by measuring the number of the labeled nanometer carriers at the outer side of the blood-brain barrier.

The steps to verify the capacity of the drug to penetrate the blood-brain barrier are as follows.

(1) At 37° C., a cell inserter with 12 wells is immersed in a gelatin solution with a mass percentage of 2% for 30 minutes for pretreatment, and then the cell inserter is washed with D-Hank's solution twice and dried.

It should be noted that, epithelial vascular cells in the brain are relatively dense, the epithelial vascular cells can be pretreated with the gelatin solution to make the growing cells more dense; and the D-Hank's solution is a common washing solution.

(2) 75,000 murine-derived BMVECs cells (from Beijing China-Japan Friendship Hospital) are placed in each well of the cell inserter which has an average well size of 3 cm. 1 mL of culture medium is added to the outside of the cell inserter, and cultured for 4 days (change the culture medium once every 2 days).

(3) After 4 days, a leak test is performed on the cell inserter. The culture medium outside the cell inserter is added to the inner layer. If a height difference of the liquid surface keeps unchanged for at least 4 hours and a resistance of the epithelial cells is higher than 250 Ω/cm$^2$, the model is established.

(4) Fluorescein isothiocyanate (FITC)-labeled nanometer carriers are added to the inner layer of the cell inserter to obtain a final concentration of 0.2 g/mL, and the outer side of the cell inserter is 1 mL culture medium, which is incubated at 37° C. for 12 h.

(5) 400 μL of the culture medium is taken from the outside when the incubation time is 1 h, 4 h, 8 h, and 12 h, respectively, and 400 μL of new culture medium is immediately supplemented.

(6) Using fluorescence spectrum and MALDI-TOF to detect and calculate penetration efficiency.

For example, the procedure of labelling the nanometer carrier with the fluorescein isothiocyanate (FITC) is as follows: 1 mL aqueous solution formed by the nanometer carrier (with a concentration of 1 mg/mL) is added to 50 μL of FITC (5 mg/mL). After mixing homogeneously, the mixture is placed into an incubator at 37° C., and incubated in dark for 2 h. After the labelling, is completed, trypan blue is added to the ultrafiltration tube, and the volume of the triphenyl blue accounts for 1/10 of the total volume of the ultrafiltration tube. The ultrafiltration tube is sufficiently centrifuged at 15000 rpm in a centrifuge for 10 min, and an amount of buffer solution (PBS, pH=7.2) is added in the ultrafiltration tube. The mixture is gently beaten to mix homogeneously, and then the ultrafiltration tube is sufficiently centrifuged at 15000 rpm in a centrifuge for 10 min. The above centrifuge operation is repeated several times until the blue color in the ultrafiltration tube disappears. The unlabeled FITC is completely removed so that the labelling process is completed.

For example, the process of obtaining the penetration efficiency by fluorescence spectrum is as follows: all of the nanometer carriers are fluorescently and the number of the labelled nanometer carriers is n. The number of the nanometer carriers passing through the blood-brain barrier is observed as m, so that the penetration efficiency of the nanometer carriers is calculated as m/n.

For example, it is feasible to identify whether the nanometer carriers penetrate the blood-brain barrier by MALDI-TOF.

Figure 5:
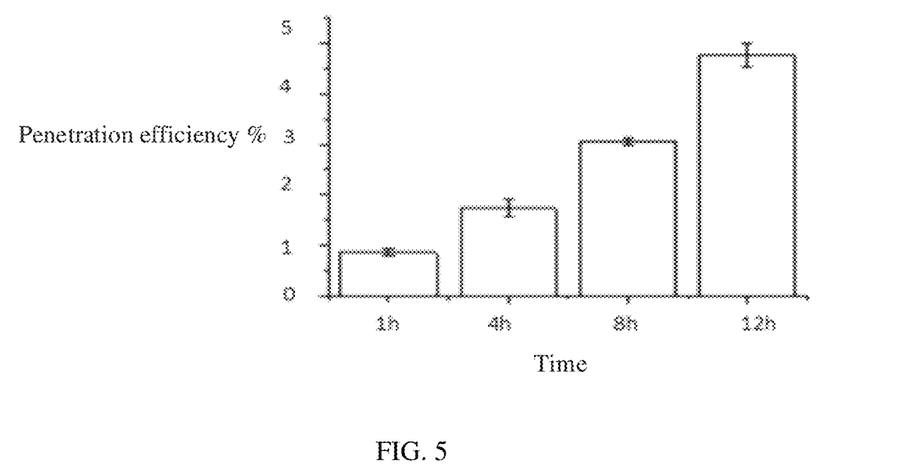
FIG. 5 is a schematic diagram of the nanometer carrier penetrating the blood-brain barrier over time provided by an embodiment of the present disclosure.

FIG. 5 is a schematic diagram of the nanometer carrier penetrating the blood-brain barrier over time provided by an embodiment of the present disclosure. As illustrated in FIG. 5, the nanometer carrier has relatively strong ability of penetrating the blood-brain barrier. When the incubation time is 1 h, the penetration amount of the nanometer carrier is 0.8%; when the incubation time is 4 h, the penetration amount of the nanometer carrier is 1.8%; when the incubation time is 8 h, the penetration amount of the nanometer carrier is 3.4%; and when the incubation time is 12 h, the penetration amount of the nanometer carrier is up to 5%.

For example, it is feasible to test binding capacity between the nanometer carrier with the peptoid compound and the EGFR protein by means of surface plasmon resonance imaging technology, and the steps are as follows.

S301: The nanometer carrier is dissolved in ddH$_2$O so that a molar concentration of the nanometer carrier solution formed is 1 to 1000 μM.

S302: Applying the samples on a surface of a 3D chip, and repeating three times for each sample, After incubation at 4° C.; for 12 hours, the chip is washed with 10× PBS. 1× PBS, and ultrapure water. Then the chip is blocked with 1M aminoethanol hydrochloride for 30 minutes and washed with 5× ultrapure water, and finally the chip is blow-dried with clean nitrogen.

Installing the chip on an SPRi instrument, measuring an SPRi angle and adjusting the SPRi angle to an optimal optical location. Relevant test points (including sample points and blank points) are selected in a detection region, and an experimental flow rate is set as 2 μL/s.

S304: Selecting PBS as the buffer solution to enter the flow cell until the baseline becomes stable. Tests are sequentially performed with the EGFR protein at a concentration of 55.6 nM, 22.8 nM, 11.4 nM, 5.70 nM and 2.85 nM. The binding time is 300 seconds, and the dissociation time is 300 seconds. Between the detection of a concentration of the EGFR protein and the detection of a next concentration of the EGFR protein, phosphoric acid was introduced for regeneration.

For example, the SPRi instrument used in the embodiments of the present disclosure is Plexera Kx5V2, Plexera Bioscience LLC, USA, which is primarily equipped with a 660 nm LED light resource, a CCD image acquisition device, and a sensor chip with microfluidic channels. The instrument displays the intensity change of the reflected light at each monitoring point over time, and records it as an SPR curve.

Figure 6:
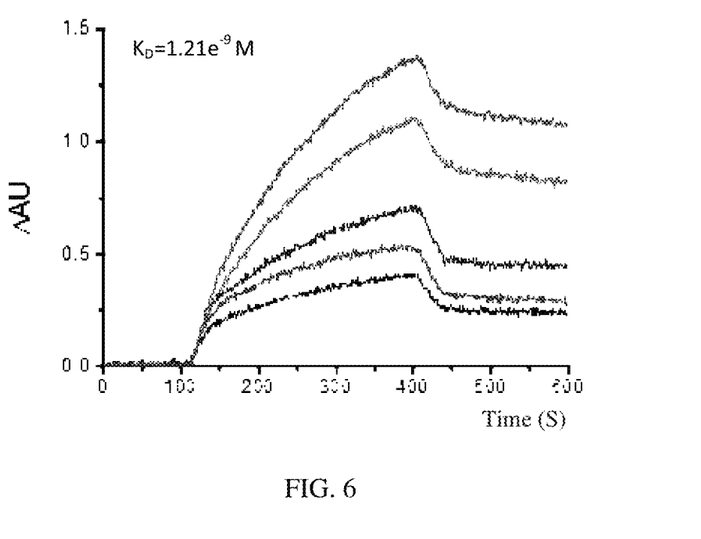
FIG. 6 is a diagram showing a result of surface plasmon resonance detection of a nanometer carrier provided by an embodiment of the present disclosure in combination with an EGFR protein at concentrations of 55.6 nM, 22.8 nM, 11.4 nM, 5.70 nM and 2.85 nM.

FIG. 6 shows a result of surface plasmon resonance detection of a nanometer carrier in combination with an EGFR protein at concentrations of 55.6 nM, 22.8 nM, 11.4 nM, 5.70 nM and 2.85 nM provided by an embodiment of the present disclosure. ΔAU represents an intensity of the binding signal calculated by deducting a baseline signal of the initial PBS buffer from the binding signal after the mobile phase passes the array, and the curve is obtained from a measurement of PlexArray HT. After fitting by BIA evaluation version 4.1 software (biacore, Inc.), the equilibrium dissociation constant $K_D$ is $1.21 \times 10^{-9}$ mol/L, which indicates that the nanometer carrier has a fairly high affinity to the EGFR protein, and can be used as a drug carrier targeting the EGFR tumors for the relevant studies.

For example, in the preparation method provided by the embodiments of the present disclosure, the nanometer carrier is prepared by chemical synthesis, and the nanometer carrier has high purity, low molecular weight, high specificity, and no immunogenicity, as well as safety and reliability.

At least one embodiment of the present disclosure further provides a pharmaceutical composition, and the pharmaceutical composition comprises the nanometer carrier of any one of the embodiments, as well as a pharmaceutically acceptable adjuvant.

For example, the adjuvant can be any one of excipients, diluents, carriers, flavoring agents, adhesives, and fillers, or any combination of at least two of the above substances. It is not limited in the embodiments of the present disclosure. The above mentioned adjuvant and the manometer carrier constitute a new and more efficient pharmaceutical composition.

It should be noted that, the adjuvant refers to other ingredient(s) except the main drug, and is non-therapeutic.

The carriers included in the adjuvant generally refer to a medicament-carrying system in the medicament delivery system, such as liposomes, starch microspheres, and albumin microspheres. For example, the pharmaceutical composition has significant targeting effect to the tumor marker EGFR protein and high selectivity. Meanwhile, it has high medicament-loading efficiency and almost no toxicity, and substantially increases the safety of the drug carrier, and thus provides a new choice for the diagnosis and treatment of EGFR-overexpressing gliomas or brain metastases of lung cancer.

At least one embodiment of the present disclosure further provides use of the pharmaceutical composition of any one of the above mentioned embodiments in the preparation of a medicament for the treatment of a disease related to human epidermal growth factor receptor 1 (EGFR).

For example, the embodiments of the present disclosure further provide use of the above mentioned pharmaceutical composition for image detecting or prognosis monitoring of EGFR protein-associated diseases.

For example, in the use provided by at least one embodiment of the present disclosure, diseases associated with the human epidermal growth factor receptor 1 (EGFR) include gliomas and brain metastases of lung cancer.

The peptoid compound and the method of preparing the peptoid compound, the nanometer carrier, the pharmaceutical composition, and the use of the pharmaceutical composition in the preparation of a medicament for the treatment of a disease related to human epidermal growth factor receptor 1 (EGFR) provided by embodiments of the present disclosure provide at least one of the following benefits:

(1) In the peptoid compound provided by at least one embodiment of the present disclosure, the peptoid compound has a high affinity to the EGFR protein, a strong target effect to the EGFR protein, and a high selectivity. At the same time, the peptoid compound has a high drug loading efficiency without toxicity, and the security is improved. Therefore, targeted drug delivery and location imaging can be realized by recognizing the EGFR protein. It provides a new choice for the diagnosis and treatment of gliomas with high expression of EGFR, brain metastasis of lung cancer and other EGFR positive tumors, and further provides in vivo data support for sequencing and digital PCR results. New and more effective targeted anticancer drugs can be made by adding a pharmaceutically acceptable excipient or adjuvant.

(2) In the nanometer carrier provided by at least one embodiment of the present disclosure, the nanometer carrier has a strong binding capacity to the EGER protein, and the equilibrium dissociation constant $K_D$ of the binding kinetic constant between the nanometer carrier and the EGFR protein is determined as $1.21 \times 10^{-9}$ mol/L by means of surface plasmon resonance technology.

(3) The method of synthesizing the peptoid compound and the nanometer carrier provided by at least one embodiment of the present disclosure is simple, and has a high production efficiency and a low production cost.

It should be noted that, without conflict, the embodiments of the present disclosure and the features in the embodiments may be combined with each other to obtain new embodiments.

What is described above is related to only the illustrative embodiments of the present disclosure and not limitative to the protection scope of the present application. The protection scope of the present application shall be defined by the accompanying claims.

What is claimed is:

1. A peptoid compound, comprising: a cysteine (Cys) subunit, a 1,4-butanediamine (Nlys) subunit, a piperonylamine subunit, a β-alanine subunit, and a 1-naphthylamine subunit, wherein the peptoid compound comprises the subunits in a sequence of: cysteine (Cys) subunit-1,4-butanediamine (Nlys) subunit-1,4-butanediamine (Nlys) subunit-piperonylamine subunit-1,4-butanediamine (Nlys) subunit-β-alanine subunit-1-naphthylamine subunit, and wherein the Cys subunit is a non-peptoid subunit where the Cys side chain is attached to the α-carbon.

2. The peptoid compound according to claim 1, wherein the peptoid compound has a structure as represented by:

Formula I

3. A preparation method of the peptoid compound according to claim 1, wherein the method comprises linking the subunits by a solid-phase synthesis process.

4. The method according to claim 3, wherein the method comprises:
  (1) linking a first subunit of the peptoid compound onto a solid-phase carrier in accordance with the linking sequence of the subunits of the peptoid compound;
  (2) reacting bromoacetic acid or bromoacetyl chloride with an amino group of the first subunit linked onto the solid-phase carrier to form an amide bond;
  (3) reacting a donor for a second subunit of the peptoid compound with a product obtained from step (2) to replace a bromine atom, and complete the linking of the second subunit;
  (4) repeating steps (2) and (3) until all subunits are linked; and
  (5) cleaving the synthesized peptoid compound from the solid-phase carrier to obtain the peptoid compound.

5. A nanometer carrier, comprising:
  the peptoid compound according to claim 1, a polyamidoamine dendrimer (PAMAM), and polyethylene glycol (PEG), wherein the polyethylene glycol (PEG) links the peptoid compound to the polyamidoamine dendrimer (PAMAM).

6. The nanometer carrier according to claim 5, wherein a molar ratio of the peptoid compound to the polyamidoamine dendrimer (PAMAM) is from 1:5 to 1:1, and a molar ratio of the PEG to the PAMAM is from 1:25 to 1:35.

7. The nanometer carrier according to claim 5, wherein a generation number of the polyamidoamine dendrimer (PAMAM) is 4 or greater than 4.

8. A pharmaceutical composition, comprising:
  the nanometer carrier according to claim 4; and
  a pharmaceutically acceptable adjuvant.

9. The pharmaceutical composition according to claim 8, wherein the pharmaceutically acceptable adjuvant comprises any one or at least two of an excipient, a diluent, a carrier, a flavoring agent, an adhesive, and a filler.

10. A method of using a nanometer carrier to prepare a medicament for the treatment of a disease related to human epidermal growth factor receptor 1 (EGFR), wherein the method comprises a step of combining the nanometer carrier of claim 5 with a pharmaceutically acceptable adjuvant.

11. The method according to claim 10, wherein the disease comprises glioma and brain metastases of lung cancer.

* * * * *